United States Patent
Kuypers et al.

(10) Patent No.: US 8,273,526 B2
(45) Date of Patent: Sep. 25, 2012

(54) METHOD OF ISOLATING STEM AND PROGENITOR CELLS FROM PLACENTA

(75) Inventors: Frans A. Kuypers, El Cerrito, CA (US); Vladimir B. Serikov, Emeryville, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 185 days.

(21) Appl. No.: 12/601,728

(22) PCT Filed: Jun. 13, 2008

(86) PCT No.: PCT/US2008/007381
§ 371 (c)(1),
(2), (4) Date: May 18, 2010

(87) PCT Pub. No.: WO2008/156659
PCT Pub. Date: Dec. 24, 2008

(65) Prior Publication Data
US 2010/0248206 A1   Sep. 30, 2010

Related U.S. Application Data

(60) Provisional application No. 60/936,237, filed on Jun. 18, 2007.

(51) Int. Cl.
*A01N 1/00* (2006.01)
*A01N 1/02* (2006.01)
*C12N 5/00* (2006.01)
*C12N 5/02* (2006.01)

(52) U.S. Cl. ......... 435/1.2; 435/325; 435/378; 435/379; 435/1.3

(58) Field of Classification Search .......... None
See application file for complete search history.

(56) References Cited

U.S. PATENT DOCUMENTS

| | | |
|---|---|---|
| 3,862,002 A | 1/1975 | Sanders |
| 5,486,359 A | 1/1996 | Caplan |
| 5,583,131 A | 12/1996 | Bridger et al. |
| 5,658,560 A | 8/1997 | Serikov |
| 5,807,686 A | 9/1998 | Wagner |
| 5,942,225 A | 8/1999 | Bruder |
| 5,962,325 A | 10/1999 | Naughton |
| 6,059,968 A | 5/2000 | Wolf, Jr. |
| 6,326,019 B1 | 12/2001 | Tseng |
| 6,338,942 B2 | 1/2002 | Kraus |
| 6,461,645 B1 | 10/2002 | Boyse et al. |
| 7,029,666 B2 | 4/2006 | Bruder |
| 7,045,148 B2 | 5/2006 | Hariri |
| 7,118,746 B1 | 10/2006 | Naughton |
| 7,147,626 B2 | 12/2006 | Goodman et al. |
| 7,160,274 B2 | 1/2007 | Ciok et al. |
| 7,183,273 B2 | 2/2007 | Bridger et al. |
| 7,255,879 B2 | 8/2007 | Hariri |
| 7,311,905 B2 | 12/2007 | Hariri |
| 7,399,632 B2 | 7/2008 | Simmons |
| 7,413,734 B2 | 8/2008 | Mistry |
| 7,468,276 B2 | 12/2008 | Hariri |
| 7,498,171 B2 | 3/2009 | Hariri |
| 7,510,873 B2 | 3/2009 | Mistry |
| 7,524,489 B2 | 4/2009 | Messina |
| 7,534,606 B2 | 5/2009 | Chen |
| 7,547,564 B2 | 6/2009 | Lee et al. |
| 7,560,276 B2 | 7/2009 | Harmon |
| 2002/0123141 A1* | 9/2002 | Hariri ........................ 435/366 |
| 2003/0235563 A1 | 12/2003 | Strom |
| 2004/0048372 A1 | 3/2004 | Hariri |
| 2004/0107453 A1 | 6/2004 | Furcht |
| 2004/0136967 A1 | 7/2004 | Weiss |
| 2004/0161419 A1 | 8/2004 | Strom |
| 2005/0054093 A1 | 3/2005 | Haas |
| 2005/0058631 A1 | 3/2005 | Kihm et al. |
| 2005/0124003 A1 | 6/2005 | Atala |
| 2005/0176139 A1 | 8/2005 | Chen |
| 2006/0154366 A1 | 7/2006 | Brown |
| 2006/0154367 A1 | 7/2006 | Kihm |
| 2006/0166361 A1* | 7/2006 | Seyda et al. ................ 435/366 |
| 2006/0171930 A1 | 8/2006 | Sayda |
| 2006/0188983 A1 | 8/2006 | Harris |
| 2006/0194776 A1 | 8/2006 | Losordo et al. |
| 2006/0222634 A1 | 10/2006 | Clarke |
| 2006/0233765 A1 | 10/2006 | Messina |
| 2006/0233766 A1 | 10/2006 | Messina |
| 2006/0234376 A1 | 10/2006 | Mistry |
| 2006/0257842 A1 | 11/2006 | Pettegrew et al. |
| 2006/0281178 A1 | 12/2006 | Sakuragawa |
| 2007/0009880 A1 | 1/2007 | Toledo et al. |

(Continued)

FOREIGN PATENT DOCUMENTS

DE   36 08 329 A1   9/1987

(Continued)

OTHER PUBLICATIONS

Sommer et al. Exp Toxic Pathol 1999; 51: 229-234.*

(Continued)

*Primary Examiner* — Chris R Tate
*Assistant Examiner* — Douglas F White
(74) *Attorney, Agent, or Firm* — Paula A. Borden; Bozicevic, Field & Francis LLP.

(57) ABSTRACT

The present invention provides methods of cryopreserving stem and progenitor cells in a mammalian placenta; and methods of obtaining fetal stem and progenitor cells from a cryopreserved mammalian placenta. Cells obtained by carrying out the methods can be used in a variety of therapeutic applications.

18 Claims, 4 Drawing Sheets

U.S. PATENT DOCUMENTS

| | | | |
|---|---|---|---|
| 2007/0053888 A1 | 3/2007 | Hariri | |
| 2007/0072293 A1 | 3/2007 | Kole | |
| 2007/0092497 A1 | 4/2007 | Hariri | |
| 2007/0134210 A1* | 6/2007 | Heidaran | 424/93.7 |
| 2007/0190034 A1 | 8/2007 | Paludan | |
| 2007/0190042 A1 | 8/2007 | Edinger | |
| 2007/0275362 A1 | 11/2007 | Edinger | |
| 2008/0032401 A1 | 2/2008 | Edinger | |
| 2008/0131410 A1 | 6/2008 | Hariri | |

FOREIGN PATENT DOCUMENTS

| | | |
|---|---|---|
| WO | WO 00/73421 A2 | 12/2000 |
| WO | WO/2005/001079 | 1/2005 |
| WO | WO/2005/001080 | 1/2005 |
| WO | WO/2005/003334 | 1/2005 |
| WO | WO/2006/071777 | 6/2006 |
| WO | WO/2006/071778 | 6/2006 |
| WO | WO/2006/071794 | 6/2006 |
| WO | WO/2006/071802 | 6/2006 |
| WO | WO/2006/071773 | 7/2006 |
| WO | WO/2008/019148 | 2/2008 |
| WO | WO/2008/109816 | 7/2008 |
| WO | WO/2008/100498 | 8/2008 |
| WO | WO/2008/156659 | 12/2008 |

OTHER PUBLICATIONS

Chen et al. Blood, May 1, 2006, vol. 107, No. 9.*
In't Anker Pieternella S. et al. Isolation of mesenchymal stem cells of fetal or maternal origin from human placenta. Stem Cells, 2004, vol. 22, No. 7, pp. 1338-1345.
Fauza. Amniotic fluid and placental stem cells. Best Pract Res Clin Obstet Gynaecol. Dec. 2004;18(6):877-91.
Steigman, et al. Isolation of mesenchymal stem cells from amniotic fluid and placenta. Current Protocols in Stem Cell Biology, 2007, Chapter 1, pp. 1E.2.1-1E.2.12.
Kaviani et al. The placenta as a cell source in fetal tissue engineering. J Pediatr Surg. Jul. 2002;37(7):995-9; discussion 995-9.
Mikkola, et al. Placenta as a site for hematopoietic stem cell development. Exp Hematol. Sep. 2005;33(9):1048-54.
Sommer, et al. Cell cultures from cryopreserved renal biopsies and other tissue samples. Exp Toxicol Pathol. May 1999:51(3):229-34.
Jin, et al. Differentiation of two types of mobilized peripheral blood stem cells by microRNA and cDNA expression analysis. J Transl Med. Jul. 22, 2008;6:39.
Serikov Vladimir et al. Human term placenta as a source of hematopoietic cells. Experimental Biology and Medicine; 234:813-823, 2009.

* cited by examiner

METHOD OF ISOLATING STEM AND PROGENITOR CELLS FROM PLACENTA

CROSS-REFERENCE

This application claims the benefit of U.S. Provisional Patent Application No. 60/936,237, filed Jun. 18, 2007, which application is incorporated herein by reference in its entirety.

BACKGROUND

Human stem cells are totipotent or pluripotent precursor cells capable of generating a variety of mature human cell lineages. The use of such cells in various therapeutic applications holds promise for clinical applications such as in regenerative medicine and in tissue/organ replacement. Currently, sources of stem cells are limited. Embryonic stem cells, which are derived from embryos, are difficult to produce in significant numbers for practical purposes; current procedures for growth and maintenance in an undifferentiated state of such cells are complex and cumbersome.

Following birth, a mammalian placenta becomes a nonfunctional organ and is typically discarded. The placenta contains multiple stem cells and other multipotent cells. For example, placenta-derived multipotent cells have been reported to differentiate into mesodermal lineage cells, including adipocytes and osteoblasts; neural lineage cells; and endodermal lineage cells such as hepatocytes.

Umbilical cord blood ("cord blood") is a source of hematopoietic progenitor stem cells. Stem cells from cord blood are currently cryopreserved for use in hematopoietic reconstitution, a widely used therapeutic procedure used in bone marrow and other related transplantations. Cord blood from a newborn individual is cryopreserved and stored for possible future use in the same individual at a later time. Because the cord blood cells are generally used to treat the same individual from which they were obtained (i.e., the donor and recipient are the same individual), the "donor" cord blood cells have the same human leukocyte antigens (HLA) as the "recipient" individual; therefore, there is no danger of transplant rejection or graft-versus-host disease.

The major drawback of cord blood as a source of stem cells is its small volume, and therefore, limited number of stem cells. A cord blood unit is typically about 100 ml, which is sufficient for successful transplantation only in children, as it contains on average about 2 million hematopoietic stem cells. Transplantation in an adult human generally requires at least $2\times10^5$ stem cells per kg, which makes cord blood sample an inadequate source for situations in which higher cell numbers are required.

There is a need in the art for methods for long-term storage of placental tissue; and for improved methods for obtaining ample numbers of stem and progenitor cells from placenta which has been cryopreserved.

Literature

U.S. Pat. Nos. 7,045,148; 7,147,626; 6,059,968; 6,461,645; 7,160,724; U.S. Patent Publication No. 2007/0053888; U.S. Patent Publication No. 2005/0176139; U.S. Patent Publication No. 2005/0058631; U.S. Patent Publication No. 2007/0009880; U.S. Patent Publication No. 2006/0257842; U.S. Pat. Nos. 5,583,131; 7,183,273.

SUMMARY OF THE INVENTION

The present invention provides methods of cryopreserving stem and progenitor cells in a mammalian placenta; and methods of obtaining fetal stem and progenitor cells from a cryopreserved mammalian placenta. Cells obtained by carrying out the methods can be used in a variety of therapeutic applications.

DEFINITIONS

As used herein, the term "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type.

The term "binds specifically," in the context of antibody binding, refers to high avidity and/or high affinity binding of an antibody to a specific polypeptide i.e., epitope of a polypeptide, e.g., an adhesion molecule. For example, antibody binding to an epitope on a specific adhesion molecule or fragment thereof is stronger than binding of the same antibody to any other epitope, particularly those which may be present in molecules in association with, or in the same sample, as the specific adhesion molecule of interest, e.g., binds more strongly to a specific adhesion molecule than to any other epitopes so that by adjusting binding conditions the antibody binds almost exclusively to the specific adhesion molecule epitope and not to any other epitope, or to any other polypeptide which does not comprise the epitope. The epitope recognized by the specific antibody can include amino acids, carbohydrates, sugars, or a combination of one or more of the foregoing. Antibodies that bind specifically to a polypeptide (e.g., to an adhesion molecule) may be capable of binding other polypeptides at a weak, yet detectable, level (e.g., 10% or less of the binding shown to the polypeptide of interest). Such weak binding, or background binding, is readily discernible from the specific antibody binding to a target polypeptide, e.g. by use of appropriate controls. In general, specific antibodies bind to a given polypeptide with a binding affinity of $10^{-7}$ M or more, e.g., $10^{-8}$ M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" means the amount of a compound or a number of cells that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a stem cell" includes a plurality of such stem cells and reference to "the progenitor cell" includes reference to one or more progenitor cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods for cryopreserving mammalian placenta; methods for cryopreserving fetal stem/progenitor cells in a mammalian placenta; and methods for obtaining a population of fetal cells from a cryopreserved mammalian placenta, where the fetal cell population comprises stem and/or progenitor cells. A subject method of cryopreserving a mammalian placenta generally involves perfusing a mammalian placenta, via arterial perfusion, with a cryopreservative solution comprising at least an anti-coagulant, a vasodilator, and at least one cryopreservative agent. The cryopreservative solution-perfused placenta is frozen and stored at a temperature below 0° C., and can be stored for days, weeks, months, or years.

Cryopreservation of a mammalian placenta, e.g., a human placenta, is of interest in clinical settings in which placental stem and/or progenitor cells may be required for future use in an individual, e.g., days, weeks, months, or years after the individual is born. The cells obtained from the cryopreserved placenta are largely not maternal; instead, they originate from the fetus. Because the "donor" source of the cells obtained from the placenta is the same as the prospective recipient individual, the possibility of rejection of the cells by the recipient is reduced or eliminated.

Stem/progenitor cells can be obtained from a cryopreserved placenta in large numbers, e.g., therapeutically effective numbers of cells. Furthermore, stem/progenitor cells obtained from a cryopreserved placenta can provide a variety of stem/progenitor cells and/or differentiated cell types, including, e.g., hematopoietic stem cells, neural progenitor cells, mesenchymal stem cells, etc.

Methods of Cryopreserving Stem/Progenitor Cells in a Mammalian Placenta

The present invention provides methods for cryopreserving fetal stem and progenitor cells in a mammalian placenta. The methods generally involve: a) perfusing a mammalian placenta with a perfusion solution comprising an anti-coagulant, a vasodilator, and a cryopreservative agent; and b) freezing the perfused placenta at a temperature below 0° C.

In some embodiments, a placenta is obtained following birth, e.g., from one minute to about one hour following birth. For example, a mammalian placenta is obtained from about one minute to about 5 minutes, from about 5 minutes to about 10 minutes, from about 10 minutes to about 20 minutes, from about 20 minutes to about 30 minutes, from about 30 minutes to about 45 minutes, or from about 45 minutes to about 60 minutes following birth.

Once the placenta is obtained, the artery and the vein of the placenta are cannulated and connected to a perfusion circuit. A perfusion circuit can include a pump and a reservoir, and may further include a heat exchange unit and/or a blood oxygenator.

The perfusion can be carried out at a temperature of from about 4° C. to about 37° C., e.g., from about 4° C. to about 10° C., from about 10° C. to about 15° C., from about 15° C. to about 17° C., from about 17° C. to about 20° C., from about 20° C. to about 22° C., from about 22° C. to about 25° C., from about 25° C. to about 30° C., or from about 30° C. to about 37° C. In some embodiments, the perfusion is carried out at room temperature, e.g., from about 17° C. to about 25° C., e.g., from about 17° C. to about 20° C., from about 20° C. to about 22° C., or from about 22° C. to about 25° C.

The perfusion solution includes an anti-coagulant, a vasodilator, and a cryopreservative agent. The perfusion solution can also include one or more of dissolved oxygen, carbon dioxide, and an inert gas.

Suitable anti-coagulants include, but are not limited to, heparin, e.g., unfractionated heparin, low molecular weight heparin (e.g., Lovonox, Fragmin, Anti-XA, Axrista, etc.); ethylenediamine tetraacetic acid (EDTA); hirudin, a hirudin analog, refludin (Refludan, recombinant hirudin), bivalirudin (Angiox); a coumarin, e.g., warfarin (4-hydroxycoumarin), (e.g., warfarin sodium, also known as Coumadin®; see, e.g., U.S. Pat. No. 6,512,005), a coumarin analog (see, e.g., U.S. Pat. No. 7,179,838); a thrombin inhibitor; a coagulation factor inhibitor; a protein C pathway component; a tissue factor pathway inhibitor; an anti-platelet compound; a vitamin K antagonist; a platelet aggregation inhibitor; a fibrinolytic pathway component; acetylsalicylic acid; and the like For example, suitable anti-coagulants include, e.g., acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluidione, heparin, hirudin, lyapolate sodium, oxazidione, penstosam polysulfate, phenindione, phenprocoumon, phosvitin, picotamide, tioclomarol, and warfarin. Suitable anti-coagulants include those that, at the concentrations/amounts used, do not have significant adverse effects on the viability of a stem/progenitor cell present in the placenta.

A suitable amount of an anti-coagulant can be in a range of from about 1 U/ml to about 100 U/ml, e.g., from about 1 U/ml to about 5 U/ml, from about 5 U/ml to about 10 U/ml, from about 10 U/ml to about 20 U/ml, from about 20 U/ml to about 30 U/ml, from about 30 U/ml to about 50 U/ml, from about 50 U/ml to about 75 U/ml, or from about 75 U/ml to about 100 U/ml.

Suitable vasodilators include, but are not limited to, papaverin, moxaverin, hydralazine (e.g., hydralazine hydrochloride; 1-hydrazinophthalazine monohydrochloride; Apresoline®), dihydralazine, minoxidil (3-hydroxy-2-imino-6-(1-piperidyl)pyrimidin-4-amine), nitroglycerin, isosorbide dinitrate, diazoxide, nitroprusside, diltiazem, amiodarone, isoxsuprine, nylidrin, tolazoline (2-benzyl-4,5-dihydro-1H-imidazole), and verapamil. Suitable vasodilators include those that, at the concentrations/amounts used, do not have significant adverse effects on the viability of a stem/progenitor cell present in the placenta.

Suitable cryopreservative agents include, but are not limited to, propylene glycol; dimethyl sulfoxide (DMSO); formamide; glycerol; polyvinylpyrrolidone (e.g., PVP-40); polyethylene glycol; as polyvinyl alcohol/polyvinyl acetate copolymer; an amphipathic phospholipid-derived phosphodiester, e.g., glycerophosphocholine (GPC), serine ethanolamine phosphodiester, glycerophosphoinositol, diphosphotriglycerol, etc.; an amphipathic osmolyte, e.g., betaine, taurine, acetyl-L-carnitine, etc.; a polyol sugar such as myo-inositol or trehalose; and the like. Two or more cryopreservative agents can be used in combination. Suitable cryopreservative compositions include, e.g., a cryopreservative agent composition as described in U.S. Patent Application No. 2007/0009880; Viaspan (DuPont; see, e.g., U.S. Pat. Nos. 4,798,824, 4,879,283; and 4,873,230); histidine-tryptophan-ketoglutarate (HTK) solution (Custodiol); a cryopreservative solution as described in U.S. Pat. No. 7,220,538; and the like.

As noted above, the perfusion solution can also include one or more of dissolved oxygen, carbon dioxide, and an inert gas. Suitable inert gases include, e.g., e.g. helium, argon, krypton, and xynon. The oxygen tension can be in the range of from about 10 mm Hg to about 200 mm Hg, e.g., from about 10 mm Hg to about 25 mm Hg, from about 25 mm Hg to about 50 mm Hg, from about 50 mm Hg to about 75 mm Hg, from about 75 mm Hg to about 100 mm Hg, from about 100 mm Hg to about 125 mm Hg, from about 125 mm Hg to about 150 mm Hg, from about 150 mm Hg to about 175 mm Hg, or from about 175 mm Hg to about 200 mm Hg.

In some embodiments, the perfusion solution can further comprise one or more of an anti-microbial agent, a growth factor, a cytokine, and an anti-oxidant.

Suitable anti-microbial agents include, but are not limited to, agents that inhibit growth and/or viability of Gram positive bacteria; agents that inhibit growth and/or viability of Gram negative bacteria; agents that inhibit growth and/or viability of acid-fast bacilli (e.g., mycobacteria); agents that inhibit growth and/or viability of a yeast or fungal cell; agents that inhibit growth and/or viability of a protozoa; and the like. Suitable anti-microbial agents include, but are not limited to, β-lactam antibiotics, e.g., penicillin, derivatives and analogs of penicillin, cephalosporin, etc.; carbapenems; aminoglycosides, e.g., streptomycin, kanamycin, and the like; macrolide antibiotics, e.g., erythromycin, tylosin, etc.; bacitracin; gramicidin; mupirocin; chloramphenicol; thiamphenicol; fusidate sodium; lincomycin; clindamycin; novobiocin; polymyxins; rifamycins; spectinomycin; tetracyclines; vancomycin; teicoplanin; streptogramins; anti-folate agents including sulfonamides, trimethoprim and its combinations and pyrimethamine; synthetic antibacterials including nitrofurans, methenamine mandelate and methenamine hippurate, nitroimidazoles, quinolines, fluoroquinolones, isoniazid, ethambutol, pyrazinamide, para-aminosalicylic acid (PAS), cycloserine, capreomycin, ethionamide, prothionamide, thiacetazone and viomycin. Suitable anti-microbial agents include those that, at the concentrations/amounts used, do not have significant adverse effects on the viability of a stem/progenitor cell present in the placenta.

Suitable cytokines and/or growth factors that can be included in the perfusion solution include, but are not limited to, a colony-stimulating factor, e.g., colony-stimulating factor-1, granulocyte colony-stimulating factor (G-CSF), granulocyte-macrophage colony-stimulating factor (GM-CSF), megakaryocyte colony-stimulating factor; an interferon, e.g., interferon-α (IFN-α), consensus interferon, IFN-β, IFN-γ, and the like; an interleukin, e.g., IL-1α, IL-1β, IL-2, IL-3, IL-4, IL-5, IL-6, IL-10, IL-11, IL-13, and the like; a stem cell factor; leukemia inhibitory factor (LIF); oncostatin M (OSM); erythropoietin; thrombopoietin; etc.

In some embodiments, the perfusion solution includes one or more anti-oxidants for reduction of oxidative stress that may occur during thawing. Suitable anti-oxidants include, but are not limited to, N-acetyl-cysteine; glutathione; vitamin C; vitamin E; and an enzyme such as a catalase, a superoxide dismutase, a peroxidase, and a peroxiredoxin.

The volume of the perfusion solution that is used ranges from about 25 ml to about 1000 ml, e.g., from about 25 ml to about 50 ml, from about 50 ml to about 100 ml, from about 100 ml to about 200 ml, from about 200 ml to about 300 ml, from about 300 ml to about 400 ml, from about 400 ml to about 500 ml, from about 500 ml to about 600 ml, from about 600 ml to about 700 ml, from about 700 ml to about 800 ml, from about 800 ml to about 900 ml, or from about 900 ml to about 1000 ml.

The perfusion solution can be perfused into an artery leading to the placenta at a rate of from about 10 ml/minute to about 500 ml/minute, e.g., from about 10 ml/minute to about 25 ml/minute, from about 25 ml/minute to about 50 ml/minute, from about 50 ml/minute to about 75 ml/minute, from about 75 ml/minute to about 100 ml/minute, from about 100 ml/minute to about 125 ml/minute, from about 125 ml/minute to about 150 ml/minute, from about 150 ml/minute to about 175 ml/minute, from about 175 ml/minute to about 200 ml/minute, from about 200 ml/minute to about 250 ml/minute, from about 250 ml/minute to about 300 ml/minute, from about 300 ml/minute to about 350 ml/minute, from about 350 ml/minute to about 400 ml/minute, from about 400 ml/minute to about 450 ml/minute, or from about 450 ml/minute to about 500 ml/minute.

As noted above, a mammalian placenta is perfused with a perfusion solution at a temperature of from about 4° C. to about 37° C. Following perfusion of the placenta with the perfusion solution, the temperature at which the placenta is held is slowly reduced to 0° C. For example, the temperature is reduced at a rate of from about 0.5° C./minute to about 5°/minute, e.g., from about 0.5° C./minute to about 1° C./minute, from about 1° C./minute to about 1.5° C./minute, from about 1.5° C./minute to about 2° C./minute, from about 2° C./minute to about 3° C./minute, from about 3° C./minute to about 4° C./minute, or from about 4° C./minute to about 5° C./minute. Finally, the perfused placenta is stored at a temperature of from about minus 50° C. (50° C.) to about minus 180° C. (180° C.), e.g., from about ⁻50° C. to about ⁻100° C., from about ⁻100° C. to about ⁻150° C., or from about ⁻150° C. to about ⁻180° C. For example, the perfused placenta can be stored in liquid nitrogen.

The perfused placenta can be stored in any suitable storage container, e.g., a sterile storage container. The storage container can include information such as the identity of the neonate and/or the mother from whom the placenta was obtained; the date on which the placenta was obtained; the composition of the perfusion solution; and the like. The information can be included in a variety of media, including, e.g., in printed form on paper or other medium; in bar-code form; in digital form, e.g., on a chip or other suitable medium; etc. The information can also be stored remotely from the container, e.g., on a computer-readable medium such as a chip or other digital information storage medium.

The perfused and cryopreserved mammalian placenta comprises fetal stem/progenitor cells. Fetal stem/progenitor cells that can be cryopreserved within a mammalian placenta using a subject method include, but are not limited to, hematopoietic stem cells (HSCs), mesenchymal stem cells (MSCs), neural stem cells, placental multipotent cells (PD-MCs), and embryonic-like stem cells.

A perfused and cryopreserved mammalian placenta can comprise from about $10^6$ fetal stem/progenitor cells to about $10^9$ fetal stem/progenitor cells, e.g., from about $10^6$ to about $5 \times 10^6$, from about $5 \times 10^6$ to about $10^7$, from about $10^7$ to about $5 \times 10^7$, from about $5 \times 10^7$ to about $10^8$, from about $10^8$ to about $5 \times 10^8$, or from about $5 \times 10^8$ to about $10^9$ fetal stem/progenitor cells.

Using an above-described method of cryopreserving fetal stem/progenitor cells in a mammalian placenta, the viability of the stem/progenitor cells present in the placenta is substantially maintained. For example, at least about 50%, at least about 60%, at least about 70%, at least about 75%, at least about 80%, at least about 85%, at least about 90%, at least about 95%, at least about 98%, or at least about 99%, of the fetal stem/progenitor cells present in the placenta before perfusion remain viable following cryopreservation as described above. For example, from about 50% to about 60%, from about 60% to about 70%, from about 70% to about 75%, from about 75% to about 80%, from about 80% to about 85%, from about 85% to about 90%, from about 90% to about 95%, from about 95% to about 98%, more than 98%, or more than 99%, of the fetal stem/progenitor cells present in the placenta before perfusion remain viable following cryopreservation as described above.

In some embodiments, the viability of at least a sub-population of stem/progenitor cells is substantially maintained following cryopreservation of stem/progenitor cells in a mammalian placenta, using a subject method. For example, in some embodiments, the viability of one or more of the following sub-populations of stem/progenitor cells is substantially maintained: hematopoietic stem cells, mesenchymal stem cells, and neural stem cells.

Methods of Obtaining Stem/Progenitor Cells from Cryopreserved Mammalian Placenta The present invention provides a method of obtaining fetal stem and progenitor cells from a cryopreserved mammalian placenta. The method generally involves: a) perfusing a cryopreserved mammalian placenta with a stem/progenitor cell collection solution comprising an agent that induces mobilization of a stem and/or progenitor cell into a blood vessel (e.g., umbilical artery or vein) of the placenta; and b) collecting the stem and/or progenitor cells from a blood vessel of the placenta (e.g., umbilical artery or vein). The mammalian placenta is one that is cryopreserved using a subject method. As such, the mammalian placenta has been perfused with a perfusion solution comprising an anti-coagulant and a vasodilating agent; has been frozen; and has been stored at a temperature below 0° C. (e.g., below ⁻50° C., as described above; e.g., at or around ⁻150° C., as described above).

To obtain fetal stem/progenitor cells from a cryopreserved mammalian placenta, the placenta is first thawed, e.g., brought to a temperature of from about 4° C. to about 37° C., e.g., from about 4° C. to about 10° C., from about 10° C. to about 15° C., from about 15° C. to about 17° C., from about 17° C. to about 20° C., from about 20° C. to about 22° C., from about 22° C. to about 25° C., from about 25° C. to about 30° C., from about 30° C. to about 34° C., or from about 34° C. to about 37° C. The cryopreserved placenta is thawed using any method, e.g., placing the storage container that is holding the cryopreserved placenta in a water bath, and bringing the placenta to a temperature of from about 4° C. to about 37° C.

The artery and vein of the thawed placenta are then cannulated, and the thawed placenta is perfused with a stem/progenitor cell collection solution comprising an agent that induces mobilization of a stem and/or progenitor cell into a blood vessel of the placenta. For example, the collection solution is perfused into the umbilical artery, and the stem/progenitor cells are collected as they exit the umbilical vein. In some embodiments, the umbilical cord has been removed, e.g., from about 50% to about 90% or more of the umbilical cord has been removed.

The thawed mammalian is perfused with the stem/progenitor cell collection solution for a period of time of from about 5 minutes to about 1 hour, e.g., from about 5 minutes to about 10 minutes, from about 10 minutes to about 15 minutes, from about 15 minutes to about 20 minutes, from about 20 minutes to about 30 minutes, from about 30 minutes to about 40 minutes, from about 40 minutes to about 50 minutes, or from about 50 minutes to about 60 minutes.

The thawed mammalian placenta is perfused with the stem/progenitor cell collection solution at a temperature of from about 4° C. to about 37° C., e.g., from about 4° C. to about 10° C., from about 10° C. to about 15° C., from about 15° C. to about 17° C., from about 17° C. to about 20° C., from about 20° C. to about 22° C., from about 22° C. to about 25° C., from about 25° C. to about 30° C., from about 30° C. to about 34° C., or from about 34° C. to about 37° C.

The stem/progenitor cell collection solution comprises an agent that induces mobilization of a stem and/or progenitor cell into a blood vessel of the placenta. Agents that induce mobilization of a stem and/or progenitor cell into a blood vessel of the placenta include, but are not limited to, a biocompatible, non-ionic surfactant (detergent); an agent that disrupts cell adhesion, e.g., ethylenediamine tetraacetic acid (EDTA); an enzyme that catalyzes the disruption of cell-cell interactions and/or that digests tissues; an antibody specific for a cell adhesion molecule, and that, when bound to the cell adhesion molecule, inhibits cell adhesion mediated by the cell adhesion molecule; and a thrombolytic enzyme.

In some embodiments, the stem/progenitor cell collection solution comprises two or more mobilization agents. For example, in some embodiments, the stem/progenitor cell collection solution comprises a biocompatible, non-ionic surfactant and an enzyme that digests tissues. In other embodiments, the stem/progenitor cell collection solution comprises a biocompatible, non-ionic surfactant and an antibody that is specific for a cell adhesion molecule and that, when bound to the cell adhesion molecule, inhibits cell adhesion mediated by the cell adhesion molecule. In other embodiments, the stem/progenitor cell collection solution comprises a biocompatible, non-ionic surfactant; an enzyme that digests tissues; and an antibody that is specific for a cell adhesion molecule and that, when bound to the cell adhesion molecule, inhibits cell adhesion mediated by the cell adhesion molecule. Other combinations of mobilization agents can be included in a stem/progenitor cell collection solution.

Thus, for example, in some embodiments, a subject method of obtaining fetal stem and progenitor cells from a cryopreserved mammalian placenta involves: a) perfusing a cryopreserved mammalian placenta with a stem/progenitor cell collection solution comprising: i) a biocompatible surfactant that induces mobilization of a stem and/or progenitor cell into a blood vessel of the placenta; and ii) an enzyme that digests tissues; and b) collecting the stem and/or progenitor cells from a blood vessel of the placenta. In an exemplary embodiment, a subject method involves a) perfusing a cryopreserved mammalian placenta with a stem/progenitor cell collection solution comprising: i) an effective amount of tyloxapol; and ii) an enzyme that digests tissues; and b) collecting the stem and/or progenitor cells from the blood vessel. In an exemplary embodiment, a subject method involves a) perfusing a cryopreserved mammalian placenta with a stem/progenitor cell collection solution comprising: i) an effective amount of AMD-3100; and ii) an enzyme that digests tissues; and b) collecting the stem and/or progenitor cells from a blood vessel of the placenta.

As another example, in some embodiments, a subject method of obtaining fetal stem and progenitor cells from a cryopreserved mammalian placenta involves: a) perfusing a cryopreserved mammalian placenta with a stem/progenitor cell collection solution comprising a biocompatible surfactant that induces mobilization of a stem and/or progenitor cell into a blood vessel of the placenta; b) collecting the stem and/or progenitor cells from a blood vessel of the placenta; c) perfusing the placenta with a stem/progenitor cell collection solution comprising an enzyme that digests tissues; and d) collecting the stem and/or progenitor cells from a blood vessel of the placenta.

In other embodiments, a subject method of obtaining fetal stem and progenitor cells from a cryopreserved mammalian placenta involves: a) perfusing a cryopreserved mammalian placenta with a stem/progenitor cell collection solution comprising a biocompatible surfactant that induces mobilization of a stem and/or progenitor cell into a blood vessel of the placenta; b) collecting the stem and/or progenitor cells from a blood vessel of the placenta; c) perfusing the placenta with a stem/progenitor cell collection solution comprising an enzyme that digests tissues, generating enzyme-digested placental tissue; d) mechanically disrupting the enzyme-digested placental tissue; and e) collecting stem/progenitor cells from the mechanically disrupted placenta.

Method of mechanically disrupting a tissue are known in the art, and any known method can be used to mechanically disrupt enzyme-digested placental tissue. Suitable methods include, e.g., mincing, blending, etc. Mechanical disruption of enzyme-digested placental tissue results in a tissue mixture that includes placental cells in suspension, and placental tissue. Tissue can be separated from the placental cells in suspension by passing the tissue mixture through one or more sieves, e.g., meshes of various pore sizes ranging from 50 μm to 500 μm. For example, the placental tissue mixture can be passed repeatedly through meshes of progressively smaller pore size, until substantially all tissue is removed, and a placental cell suspension (e.g., single-cell suspension) has been obtained.

A placental cell suspension can include, in addition to fetal stem/progenitor cells, one or more other placental cell types, including, e.g., epithelial cells (e.g., fetal chorionic cells). Placental cells other than fetal stem/progenitor cells, that are present in the placental cell suspension, can be separated from fetal stem/progenitor cells by one or more of washing; centrifugation; density gradient centrifugation; elution; positive selection; and negative selection, using well-established methods. Density gradient centrifugation includes, e.g., Ficoll Hypaque gradient centrifugation; Histopaque gradient centrifugation; and the like.

Placental cells other than fetal stem/progenitor cells, that are present in the placental cell suspension, can be separated from fetal stem/progenitor cells by positive selection, negative selection, or a combination of positive and negative selection, using methods that are well known in the art. For example, one or more antibodies specific for one or more desired fetal stem/progenitor cell types can be coupled to an insoluble support (e.g., a magnetic bead) to immobilize the antibody; the immobilized antibody can be contacted with the placental cell suspension; and a magnetic field applied, to positively select for the one or more desired fetal stem/progenitor cell types. For example, antibody to CD34 can be coupled to a magnetic bead; the immobilized antibody can be contacted with the placental cell suspension; and a magnetic field applied, to positively select for fetal HSCs. As another example, one or more antibodies specific for undesired cell types (e.g., fetal epithelial cells) can be coupled to an insoluble support (e.g., a magnetic bead) to immobilize the antibody; the immobilized antibody can be contacted with the placental cell suspension; and a magnetic field applied, to negatively select for and remove the undesired cell type(s).

Biocompatible Surfactants

A suitable "biocompatible" non-ionic surfactant is one that, at the concentration/amount used, does not substantially reduce the viability of a fetal stem/progenitor cell. Biocompatible surfactants, e.g., benzalkonium chloride, cetylpyridinium chloride, an alkylaryl polyether alcohol (e.g., tyloxapol), various polysorbates (e.g., polysorbate 80, polysorbate 20), and further polyethoxylated substances and poloxamers (e.g., poloxamer 282). Biocompatible surfactants include nonionic, cationic, ionic, and zwitterionic surfactants. Suitable non-ionic surfactants include, but are not limited to, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octoxinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters.

In some embodiments, the non-ionic surfactant is tyloxapol. Tyloxapol is a 4-(1,1,3,3-tetramethylbutyl)-phenol polymer with ethylene oxide and formaldehyde (also known as tyloxapol). Tyloxapol is also known as Triton WR-1339. In these embodiments, tyloxapol is present in the stem/progenitor cell collection solution at a concentration of from about 20 mg/L to about 500 mg/L, e.g., from about 20 mg/L to about 50 mg/L, from about 50 mg/L to about 100 mg/L, from about 100 mg/L to about 150 mg/L, from about 150 mg/L to about 200 mg/L, from about 200 mg/L to about 250 mg/L, from about 250 mg/L to about 300 mg/L, from about 300 mg/L to about 350 mg/L, from about 350 mg/L to about 400 mg/L, from about 400 mg/L to about 450 mg/L, or from about 450 mg/L to about 500 mg/L.

In other embodiments, the stem/progenitor cell mobilization agent is a CXCR4 antagonist such as AMD-3100 or a derivative or analog thereof AMD-3100 (1,1'-[1,4-phenylene-bis(methylene)]-bis-1,4,8,11-tetraazacyclotetradecane) is described in U.S. Pat. No. 5,583,131. Also suitable for use are derivatives and analogs of AMD-3100, e.g., compounds as described in U.S. Pat. Nos. 7,169,750 and 7,183,273. AMD-3100, or an analog or derivative thereof, can be present in the stem/progenitor cell collection solution at a concentration of from about 50 mg/L to about 500 mg/L, e.g., from about 50 mg/L to about 100 mg/L, from about 100 mg/L to about 150 mg/L, from about 150 mg/L to about 200 mg/L, from about 200 mg/L to about 250 mg/L, from about 250 mg/L to about 300 mg/L, from about 300 mg/L to about 350 mg/L, from about 350 mg/L to about 400 mg/L, from about 400 mg/L to about 450 mg/L, or from about 450 mg/L to about 500 mg/L.

Enzymes

Suitable enzymes that can be included in a stem/progenitor cell collection solution include enzymes that digest tissues, where suitable enzymes include, but are not limited to, a matrix metalloproteinase (e.g., a collagenase), trypsin, chymotrypsin, papain, pepsin, proteinase K, a DNAse, dispase, carboxypeptidase, calpain, and subtilisin. Suitable thrombolytic enzymes that can be included in a stem/progenitor collection solution include, but are not limited to, streptokinase, urokinase, and the like.

Antibodies that Inhibit Cell Adhesion

Antibodies that can be included in a stem/progenitor cell collection solution include an antibody that is specific for a cell adhesion molecule and that, when bound to the cell adhesion molecule, inhibits cell adhesion mediated by the cell adhesion molecule. Adhesion molecules include, e.g., an intracellular adhesion molecule (ICAM) (e.g., ICAM-1); a vascular cell adhesion molecule (VCAM; CD106), a platelet-endothelial cell adhesion molecule (PECAM); an integrin; a cadherin; and a selectin. Any antibody that specifically binds to an adhesion molecule, and that, when bound to the adhesion molecule, inhibits cell adhesion mediated by the cell adhesion, is suitable for use. Several such antibodies are known and can be used. The term "antibody" includes antibody of any of various isotypes; polyclonal antibodies; monoclonal antibodies; antigen-binding fragments of a monoclonal antibody (e.g., Fab, Fv, scFv, and Fd fragments); chimeric antibodies; humanized antibodies; single-chain antibodies; etc.

As noted above, the stem/progenitor cell collection solution comprises an agent that induces mobilization of a stem and/or progenitor cell into a blood vessel of the placenta. The stem/progenitor cell collection solution can further comprise one or more components, e.g., a growth factor; a cytokine; an agent that induces differentiation of a stem/progenitor cell; an anti-microbial agent; a growth factor; a cytokine; etc.

Suitable cytokines and/or growth factors that can be included in the perfusion solution include, but are not limited to, a colony-stimulating factor, e.g., colony-stimulating factor-1, granulocyte colony-stimulating factor (G-CSF), granulocyte-macrophage colony-stimulating factor (GM-CSF), megakaryocyte colony-stimulating factor; an interferon, e.g., interferon-α (IFN-α), consensus interferon, IFN-β, IFN-γ, and the like; an interleukin, e.g., IL-1α, IL-1β, IL-2, IL-3, IL-4, IL-5, IL-6, IL-10, IL-11, IL-13 and the like; a stem cell factor; leukemia inhibitory factor (LIF); oncostatin M (OSM); erythropoietin; thrombopoietin; etc.

Suitable anti-microbial agents include, but are not limited to, β-lactam antibiotics, e.g., penicillin, derivatives and analogs of penicillin, cephalosporin, etc.; carbapenems; aminoglycosides, e.g., streptomycin, kanamycin, and the like; macrolide antibiotics, e.g., erythromycin, tylosin, etc.; bacitracin; gramicidin; mupirocin; chloramphenicol; thiamphenicol; fusidate sodium; lincomycin; clindamycin; novobiocin; polymyxins; rifamycins; spectinomycin; tetracyclines; vancomycin; teicoplanin; streptogramins; anti-folate agents including sulfonamides, trimethoprim and its combinations and pyrimethamine; synthetic antibacterials including nitrofurans, methenamine mandelate and methenamine hippurate, nitroimidazoles, quinolines, fluoroquinolones, isoniazid, ethambutol, pyrazinamide, para-aminosalicylic acid (PAS), cycloserine, capreomycin, ethionamide, prothionamide, thiacetazone and viomycin. Suitable anti-microbial agents include those that, at the concentrations/amounts used, do not have significant adverse effects on the viability of a stem/progenitor cell present in the placenta.

The collected stem/progenitor cells are viable, e.g., at least about 80%, at least about 85%, at least about 90%, at least about 95%, at least about 98%, or at least about 99%, of the collected stem/progenitor cells are viable. Viability can be determined using any standard method, e.g., uptake of a dye such as propidium iodide, which is taken up by dead cells and not substantially by live cells.

The recovery of fetal stem/progenitor cells from the placenta is in the range of from about 50% to about 100%, e.g., from about 50% to about 60%, from about 60% to about 70%, from about 70% to about 75%, from about 75% to about 80%, from about 80% to about 85%, from about 85% to about 90%, from about 90% to about 95%, from about 95% to about 98%, or from about 98% to about 100%. For example, the proportion of the viable fetal stem/progenitor cells present in the cryopreserved mammalian placenta that are recovered using a subject method is in the range of from about 50% to about 100%, e.g., from about 50% to about 60%, from about 60% to about 70%, from about 70% to about 75%, from about 75% to about 80%, from about 80% to about 85%, from about 85% to about 90%, from about 90% to about 95%, from about 95% to about 98%, or from about 98% to about 100%.

Stem/progenitor cells collected from a cryopreserved mammalian placenta using a subject method are also referred to herein as "collected stem/progenitor cells" or "a collected stem/progenitor cell population." The collected stem/progenitor cells are substantially fetal in origin, e.g., at least about 90%, at least about 95%, at least about 98%, or at least about 99% of the stem/progenitor cells obtained using a subject method are fetal in origin. Whether the collected stem/progenitor cells are fetal can be readily ascertained by determining the identity of a major histocompatibility (MHC) antigen(s) on the surface of the stem/progenitor cells. Where the collected stem/progenitor cells are human, one can readily determine whether such cells are fetal or maternal by determining the identity of a human leukocyte antigen (HLA) on the surface of the stem/progenitor cells. An MHC (or HLA) antigen(s) can be readily detected using antibody specific for the antigen(s), where such antibodies are readily available. For example, the antibody can be detectably labeled (directly or indirectly), and binding of the detectably labeled antibody detected using any of a number of standard assays, e.g., fluorescence activated cell sorting (FACS), an immunohistochemical assay, and the like.

The number of stem/progenitor cells that can be collected (obtained) from a cryopreserved, thawed mammalian placenta ranges from about $10^6$ fetal stem/progenitor cells to about $10^9$ fetal stem/progenitor cells, e.g., from about $10^6$ to about $5\times10^6$, from about $5\times10^6$ to about $10^7$, from about $10^7$ to about $5\times10^7$, from about $5\times10^7$ to about $10^8$, from about $10^8$ to about $5\times10^8$, or from about $5\times10^8$ to about $10^9$ fetal stem/progenitor cells.

In some embodiments, the collected stem/progenitor cell population comprises hematopoietic stem cells. Hematopoietic stem cells (HSCs) are mesoderm-derived cells, and can be characterized as $CD34^+$, and may also be positive for one or more additional markers, e.g., one or more of $CD38^+$, $CD90^+$, $CD133^+$, $CD105^+$, and $CD45^+$; and can be characterized as negative for various lineage-specific markers ($lin^-$). HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In some embodiments, the collected stem/progenitor cell population comprises neural stem cells. Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining and culturing NSCs are known in the art.

In some embodiments, the collected stem/progenitor cell population comprises mesenchymal stem cells. Mesenchymal stem cells (MSC), originally derived from the embryonal mesoderm and isolated from adult bone marrow, can differentiate to form muscle, bone, cartilage, fat, marrow stroma, and tendon. MSCs can be characterized as $CD90^+$, $CD105^+$, $CD166^+$, $STRO-1^+$, and $CD73^+$; and $CD31^-$, $CD34^-$, and $CD45^-$. Methods of isolating and culturing MSC are known in the art; and any known method can be used to obtain MSC. See, e.g., U.S. Pat. No. 5,736,396, which describes isolation and culture of human MSC. See also, e.g., Fukuchi et al. ((2004) *Stem Cells* 22:649-658); and in 't Anker et al. ((2007) *Stem Cells* 22:1338-1345).

In some embodiments, the collected stem/progenitor cell population comprises multipotent placenta-derived progenitor cells, which can be induced to differentiation in vitro into a variety of cell types, e.g., adipocytes, osteoclasts, hepatocytes, etc. See, e.g., Chien et al. ((2006) *Stem Cells* 24:1759-1768).

Collected stem/progenitor cells can be further manipulated in any of a variety of ways. For example, the collected stem/progenitor cells can be sorted, to obtain a desired sub-population of cells, to remove any residual maternal cells, etc. The stem/progenitor cells can be contacted in in vitro cell culture with an agent that prevents stem cells from differentiation, or with an agent that induces a stem/progenitor cell to differentiate into a desired cell type(s). The stem/progenitor cells can be genetically modified, e.g., the stem/progenitor cells can be genetically modified with a nucleic acid comprising a nucleotide sequence encoding a growth factor, a cytokine, a blood clotting factor, or other therapeutic polypeptide. The stem/progenitor cells can be stored (e.g., cryopreserved in liquid nitrogen) for later use. In addition, two or more such manipulations can be carried out. For example, the collected stem/progenitor cells can be sorted, then cultured with an agent that induces differentiation into a desired cell type(s). As another example, the collected stem/progenitor cells can be cultured with an agent that induces differentiation, then sorted.

Methods of inducing a stem/progenitor cell to undergo differentiation in vitro are known in the art; and any known method can be used. See, e.g., Odorico et al. ((2001) *Stem Cells* 19:193-204).

A subject method can involve: a) inducing differentiation in a collected stem/progenitor cell population, generating a mixed cell population that includes undifferentiated stem/progenitor cells and differentiated cells; and b) separating the differentiated cells from the undifferentiated cells. As one example, HSCs can be induced to undergo differentiation in vitro into a variety of differentiated cells, including, e.g., neutrophils, granulocytes, macrophages, myeloid cells (e.g., B cells, T cells), etc.

As one example, a subject method can involve: a) separating HSCs from a population of collected stem/progenitor cells; and b) inducing differentiation of the HSCs into myeloid cell lineage cells, or some other lineage.

As another example, a subject method can involve: a) inducing cardiomyogenesis in a population of collected stem/progenitor cells, generating a mixed population of undifferentiated stem cells and cardiomyocytes; and b) separating cardiomyocytes from the undifferentiated (non-cardiomyocyte) cells. The separation step can involve contacting the mixed cell population with an antibody specific for a cardiomyocyte-specific cell surface marker.

Neuronal Cells and Glial Cells

For example, under certain in vitro culture conditions, a stem cell can be induced to differentiate into a neuronal cell, an astrocyte, an oligodendrocyte, or a neuronal precursor cell. As an example, a collected stem/progenitor cell (or population of collected stem/progenitor cells) can be cultured in the presence of ligands that bind growth factor receptors to promote enrichment for neural precursor cells. The growth environment may contain a neural cell supportive extracellular matrix, such as fibronectin. Other methods for inducing differentiation of a stem cell into a neuronal precursor cell are described in, e.g., U.S. Pat. Nos. 6,887,706; and 7,011,828. Markers of interest include, but are not limited to, β-tubulin III or microtubule-associated protein 2 (MAP-2), characteristic of neurons; glial fibrillary acidic protein (GFAP), present in astrocytes; galactocerebroside (GalC) or myelin basic protein (MBP); characteristic of oligodendrocytes; Nestin or Musashi, characteristic of neural precursors and other cells. A mature neuronal cell can be characterized by an ability to express one, two, three, four, five, six, seven, or all eight of: 160 kDa neuro-filament protein, MAP2ab, glutamate, synaptophysin, glutamic acid decarboxylase (GAD), tyrosine hydroxylase, GABA, and serotonin. The differentiated cells forming neural progenitor cells, neuron cells and/or glial cells can also be characterized by expressed markers characteristic of differentiating cells. The in vitro differentiated cell culture can be identified by detecting molecules such as markers of the neuroectodermal lineage, markers of neural progenitor cells, neuro-filament proteins, MAP2ab, glutamate, synaptophysin, glutamic acid decarboxylase, GABA, serotonin, tyrosine hydroxylase, β-tubulin, β-tubulin III, GABA Aα2 receptor, glial fibrillary acidic protein (GFAP), 2', 3'-cyclic nucleotide 3'-phosphodiesterase (CNPase), plp, DM-20, O4, and NG-2 staining.

Hepatocytes

As another example, a collected stem/progenitor cell (or a population of collected stem/progenitor cells) can be cultured in the presence of a hepatocyte differentiation agent to promote enrichment for hepatocyte-like cells. The growth environment may contain a hepatocyte supportive extracellular matrix, such as collagen or Matrigel™. Suitable differentiation agents include various isomers of butyrate and their analogs, exemplified by n-butyrate. The cultured cells are optionally cultured simultaneously or sequentially with a hepatocyte maturation factor, such as an organic solvent like dimethyl sulfoxide (DMSO); a maturation cofactor such as retinoic acid; or a cytokine or hormone such as a glucocorticoid, epidermal growth factor (EGF), insulin, transforming growth factors (TGF-α and TGF-β), fibroblast growth factors (FGF), heparin, hepatocyte growth factors (HGF), interleukins (IL-1 and IL-6), insulin-like growth factors (IGF-I and IGF-II), and heparin-binding growth factors (HBGF-1). Hepatocyte lineage cells differentiated from stem cells can display one, two, three, or more, of the following markers: $α_1$-antitrypsin (AAT) synthesis, albumin synthesis, asialoglycoprotein receptor (ASGR) expression, absence of α-fetoprotein, evidence of glycogen storage, evidence of cytochrome p450 activity, and evidence of glucose-6-phosphatase activity.

Cardiomyocytes

A collected stem/progenitor cell (or a population of collected stem/progenitor cells) can be induced in vitro to differentiate into a cardiomyocyte, generating a cardiomyocyte. A cardiomyocyte can be used to treat, e.g., areas of ischemic cardiac tissue resulting from myocardial infarction; heart failure; and the like. Suitable cardiomyocyte-specific cell surface markers include, but are not limited to, troponin and tropomyosin.

Mesenchymal Lineages

A collected stem/progenitor cell (or a population of collected stem/progenitor cells) can be induced in vitro to differentiate into a cell of a mesenchymal lineage, e.g., a lineage selected from osteogenic, chondrogenic, tendonogenic, ligamentogenic, myogenic, marrow stromagenic, adipogenic and dermogenic. Thus, e.g., collected stem/progenitor cells can be induced in vitro to differentiate into an osteoblast, a chondrocyte, a myoblast, a stromal cell, etc., using any known method. See, e.g., U.S. Pat. No. 5,736,396, which describes methods for in vitro differentiation of human mesenchymal stem cells.

Pancreatic Islet Cells

A collected stem/progenitor cell (or a population of collected stem/progenitor cells) can be induced in vitro to differentiate into a pancreatic islet cell, generating a pancreatic islet cell, which can be used to treat Type 1 diabetes. Methods of inducing differentiation into a pancreatic islet cell are described in, e.g., Zulewski (2006) *Swiss Med. Weekly* 136 (41-42):647-54; Trounson (2006) *Endocrin. Rev.* 27(2):208-19; Soria et al. (2005) *Novartis Found. Symp.* 265:158-67; and Xu et al. (2006) *Cloning and Stem Cells* 8:96-107.

Separation of Differentiated Cells from Undifferentiated Cells

As noted above, where a population of collected stem/progenitor cells is induced in vitro to differentiate, a mixed cell population can result, where the mixed cell population includes undifferentiated cells and differentiated cells. Where it is desired to generate a population of cells in which most or substantially all of the cells are differentiated cells, the differentiated cells can be separated from the undifferentiated cells. Separation can be carried out on the basis of cell surface markers expressed by differentiated cells, but not by undifferentiated cells. Suitable cell surface markers for differentiated cells of various cell types are known in the art, and are described above.

Separation can be carried out using well-known methods, including, e.g., any of a variety of sorting methods, e.g., fluorescence activated cell sorting (FACS), negative selection methods, etc. The selected (differentiated) cells are separated from non-selected (undifferentiated) cells, generating a population of selected ("sorted") cells. A selected cell population can be at least about 75%, at least about 80%, at least about 85%, at least about 90%, at least about 95%, at least about 98%, at least about 99%, or greater than 99% differentiated cells of a particular (selected) cell type.

Cell sorting (separation) methods are well known in the art. Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide [PI], LDS, and the like). Any technique may be employed which is not unduly detrimental to the viability of the selected cells. Where the selection involves use of one or more antibodies, the antibodies can be conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry.

Utility

A subject method of cryopreserving fetal stem and progenitor cells, and a subject method of collecting fetal stem and progenitor cells from a cryopreserved mammalian placenta, are useful for cryopreserving and obtaining fetal stem and progenitor cells, which cells find use in a variety of research and clinical applications.

Research applications include, but are not limited to, use of the cells to determine the effect of various factors on differentiation; use of the cells to identify factors that maintain pluripotency; use of the cells, e.g., in an experimental animal model, in studies of in vivo differentiation of a stem or progenitor cell; use of the cells in an experimental animal model of a disease, e.g., to determine the effect of a stem or progenitor cell on the progression of the disease; and the like.

Clinical applications of the collected cells include treatment of a disorder in an individual (e.g., a human) from whom the fetal stem/progenitor cells were obtained. For example, collected stem/progenitor cells, or progeny thereof, can be introduced into an individual in need thereof, to treat a condition or disorder. The individual can be a neonate (e.g., an individual in an age range of from about one week to about one month), an infant (e.g., an individual in an age range of from about one month to about 12 months), a toddler (e.g., an individual in an age range of from about 12 months to about 3 years), a child in an age range of from about 3 years to about 8 years, a pre-teenager (e.g., an individual in an age range of from about 9 years to about 12 years), a teenager (e.g., an individual in an age range of from about 13 years to about 19 years), an adult (e.g., an individual 20 years old or older), a geriatric patient (e.g., an individual in an age range of from about 65 years to 100 years or older); etc.

Collected stem/progenitor cells can be used to treat various hematological disorders, e.g., a hemoglobinopathy; a deficit in the number of one or more blood cell types (e.g., due to treatment for cancer; due to disease; etc.); central nervous system disorders, including, e.g., neurodegenerative diseases (e.g. Alzheimer's Disease, Parkinson's Disease, Multiple Sclerosis (MS), Huntington's Disease, Amyotrophic Lateral Sclerosis, etc.); acute brain injury (e.g. stroke, head injury, cerebral palsy); an immunodeficiency disorder; etc.

Collected stem/progenitor cells, or progeny thereof, can be used to provide tissues for grafting such as bone marrow, skin, cartilage, tendons, bone, muscle (including cardiac muscle), blood vessels, cornea, neural cells, gastrointestinal cells, etc. Collected stem/progenitor cells, or progeny thereof, can be used to regenerate one or more blood cell types, e.g., where an individual has a lower than normal number of one or more blood cell types, due to disease, or due to depletion as a result of cancer chemotherapy regimen, or other treatment.

Subjects suitable for treatment using stem/progenitor cells, or progeny thereof, collected using a subject method include individuals suffering from a disorder such as a hematological disorder; a deficit in the number of one or more blood cell types; a neurological disorder (e.g., Parkinson's disease); and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Cryopreservation of Mammalian Placenta; and Collection of Stem/Progenitor Cells from the Cryopreserved Placenta Methods Placenta perfusion and cryostorage: Following IRB approval and informed consent, human term placentas were obtained from healthy females following caesarian section at Alta Bates Hospital (Oakland, Calif.). Freshly obtained human placentas were used which have been subjected to a conventional cord blood recovery process by draining substantially all of the cord blood from the placenta. Placentas were first infused with in an anticoagulant/vasodilator solution (Heparin 30 U/ml, papaverin 0.05 mg/ml) at a temperature of 20 to 25° C. For perfusion procedures, artery and vein of umbilical cord were further cannulated, and connected to a perfusion circuit, which contains heat exchange unit, blood oxygenator, roller pump and perfusion reservoir. Blood oxygen tension and carbon dioxide tension, temperature of perfusate and perfusate flow rate were continuously monitored. Pressure in the umbilical cord artery and vein was constantly measured using Baxter pressure transducers connected to blood pressure monitor (Protocol Systems, Portland, Oreg.). Constant temperature of perfusate was maintained using heat exchange unit connected to temperature-controlled water bath.

Placenta hematopoietic $CD34^+$ and mesenchymal stem cells isolation: Part of placenta was isolated with clamps, arterial vessel washed with 50 cc phosphate buffered saline (PBS), then infused 50 cc PBS with Penicillin/Streptomycin/Fungisone (PSF), 2.5 U/ml Dispase, Trypsin (0.25 mg/ml)/ethylenediamine tetraacetate (EDTA) for 20 min at room temperature. Tissue samples were dissected, placed in PBS with 0.1% Collagenase, 2.5 U/ml Dispase for 30 min at 37° C. Tissue sample was vortexed for 5 min, then filtered through 100 micron filter.

To obtain $CD34^+$ cells tissue digest was centrifuged at 400×g for 15 min, supernatant discarded, cells resuspended in growth medium (GM): alpha-Modified Eagle's Medium (MEM) with PSF, 15% fetal calf serum (FCS), 2 mM L-glutamine. Sample was stored at 4° C. for fluorescence activated cell sorting (FACS) analyses.

To obtain mesenchymal stem cells tissue digest was centrifuged at 400×g for 15 min, supernatant discarded, cells resuspended in GM: alpha-MEM with PSF, 15% FCS, 2 mM L-glutamine. Cells placed in 60 mm Petri dishes. Dishes washed 24 hours later, washed 2×PBS, GM added. Plastic-adherent cell were further grown for 2-3 weeks in alpha-MEM with PSF, FCS, 2 mM L-glutamine.

Placenta cryopreservation: Placenta was washed with 50 ml PBS, then perfused for 20 min with cocktail of cryopreservatives: 15% propylene glycol, 14% dimethylsulfoxide (DMSO), 14% Formamide, 57% PBS, PSF. Arterial and venous lines were then closed, thermocouple inserted into center of tissue. Placenta was then placed in a plastic container and secured (closed). The closed plastic container containing the placenta was placed into a −80° C. freezer for 12 hours, then placed in liquid nitrogen.

Placenta re-warming: The plastic container containing the placenta was placed in water bath 37° C., temperature of tissue (thermocouple) monitored. After tissue temperature reached 34-36° C., the container was opened, catheters connected to pre-warmed perfusion system and perfused with PBS (PSF) changing perfusate every 10 min for 40 min.

Isolation of cell from cryopreserved placenta: Arterial vessel was washed with 50 cc PBS, then infused 50 cc PBS with PSF, 2.5 U/ml Dispase, Trypsin/EDTA (0.5 mg/ml/0.2 mg/ml) for 20 min at room temperature. Tissue samples were dissected, placed in PBS with Trypsin/EDTA (20% standard solution), 0.1% Collagenase, 2.5 U/ml Dispase for 30 min at 37° C. Tissue was vortexed for 5 min, filtered through 100 micron filter. Hematopoietic and mesenchymal stem cells were isolated as described above.

Derivation and differentiation of placenta-derived hematopoietic stem cells. Sample of placenta tissue (5 g) was thoroughly washed in 3 changes of sterile PBS (100 ml) with PSF, 30 U/ml Heparin, cut to pieces 3×3×3 mm and placed in Trypsin/EDTA solution (0.25 mg/ml Trypsin) at 37° C. for 60 min with periodic shaking. 5 ml of tissue digest was then diluted in 45 ml Dulbecco's modified Eagle's medium (DMEM) with 2% FCS, vortexed, centrifuged at 300×g for 10 min. Supernatant was discarded, tissue pellet was washed twice with the same solution. Final cell pellet was resuspended in 5 ml alpha-MEM medium with 10% FCS with PSF.

Characterization of viability and numbers of hematopoietic stem cells in cord blood and placenta tissue derivatives. The number of CD34 cells in a cell mixture was determined using the CD34 and CD45 markers. The CD34 antigen is present on immature hematopoietic precursor cells and all hematopoietic colony-forming cells in bone marrow and blood, including unipotent and pluripotent progenitor cells (Graves M F, Titley, I, Colman S M et al In: Schlossman S F Boumsell L, Gilks W et al eds Leukocyte Typing V: White cell differentiation antigens. New York N.Y.: Oxford University Press, 1995; 1: 840-846). Fluorochrome-conjugated monoclonal antibodies directed against the CD34 molecule were used to identify these cells by flow cytometry using a FACS-caliber flow cytometer (BD Bioscences, San Jose, Calif.) using the Procount Progenitor Cell Enumeration Kit (BD Bioscences, San Jose, Calif.). Multicolor analysis to identify the absolute number of viable CD34 cells in the population was applied according to a detailed protocol supplied by the manufacturer. Characterization of cell viability and counting of numbers of hematopoietic progenitors was performed by FACS. CD34-positive CD45-positive cell population was dually labeled, using kits with positive control CD34$^+$ CD45$^+$ positive fluorescent beads (BD Biosciences), according to manufacturer's protocol. CD34-CD45 positive population was gated, and viability determined by To-Pro nuclear/cytoplasm staining. Number of cells was determined as percent of total nucleated cells as well as absolute numbers per volume/mass of specimen.

Differentiation assays. Differentiation assays were performed using complete MethoCult® Methylcellulose-based media (containing 30% FCS, erythropoietin (3 U/ml), IL-3 (10 ng/ml), stem cell factor (50 ng/ml) and granulocyte-macrophage colony stimulating factor (GM-CSF) (10 ng/ml) in 30 ml plastic Petri dishes (all from Stem Cell Technologies, Canada). Cultures were incubated for 14-16 days and colonies scored for presence of colony forming unit erythroid (CFU-E), burst-forming unit erythroid (BFU-E), colony forming unit-granulocyte, macrophage (CFU-GM), and colony forming unit-granulocyte, erythroid, macrophage, megakaryocyte (CFU-GEMM).

Long-term culture-initiating cell (LTC-IC) assays. LTC-IC assays were performed using feeder layers from stromal placenta-derived cell lines isolated from of placentas in this study. Placenta-derived stromal cells were seeded in 24-well culture clusters and cultured for 2-3 days until confluence was reached in alpha-MEM medium with 10% FCS. To inactivate cells of feeder layer, cells were treated with 10 µg/ml Mitomycin C (Sigma) for 2 hours, washed 3 times with PBS. Cells isolated from placenta tissue were suspended in long-term culture medium (MyeloCult, Stem Cell Technologies, Canada) according to manufactures protocol and placed in wells with feeder layers. Cells were grown for 6 weeks in atmosphere of 5% $CO_2$ at 37° C., medium was changed weekly. After 6 week cell were lifted by trypsinization and differentiation assays were performed as described above in methylcellulose medium (MethoCult, Stem Cell technologies), containing 30% FCS, erythropoietin (3 U/ml), IL-3 (10 ng/ml), stem cell factor (50 ng/ml) and GM-CSF (10 ng/ml) in 30 ml plastic Petri dishes. Cultures were incubated for 14-16 days and colonies scored.

Derivation and differentiation of human placenta-derived stromal stem. Cells were filtered through 100 µ-pore filter, re-suspended in growth medium (GM)-alpha-MEM with 2 mM L-glutamine and 20% of fetal bovine serum (FBS) (Invitrogen) with penicilline/streptomycin. The confluent primary cultures were washed twice with PBS without $Ca^{++}Mg^{++}$ (Invitrogen). Cells will be detached following Trypsin/EDTA. Cells were re-suspended in 40 ml of the GM and cultured in 100 mm culture dishes (Costar). First two passages were performed with the cells reaching about 70-90% confluency by splitting the cells 1:1. For differentiation assays the cells were cultured at initial concentration of $2\times10^5$ ml in GM in 60 mm Petri dishes, containing sterile pieces of cover glass. Adipogenic differentiation was stimulated by seeding the cells for 3 weeks in GM supplemented with $10^{-8}$ ml/l dexamethasone and 5 µg/ml insulin. Osteogenic differentiation was induced by culturing in GM containing 10 mM β-glycerol phosphate, 50 µg/ml ascorbic acid, and $10^{-8}$ ml/l dexamethasone for 3 weeks. Neurogenic differentiation was performed by addition of retinoic acid ($10^{-7}$-$10^{-8}$ M to the medium).

Immunostaining: Tissues were fixed with 4% paraformaldehyde, washed in PBS, permeabilized with 1% Triton X-100. Slices were incubated with blocking buffer (3% BSA in 4×SCC, 0.1% Triton X-100) for 60 min at 37° C. and incubated with primary Ab (1:100 dilution) overnight at 4° C. Slices were washed, incubated with blocking solution and then incubated with secondary Ab (1:500) labeled with FITC- or Rhodamine for 60 min at 37° C., washed, mounted on slides with Antifade reagent. Paraffin sections de-paraffinized first and prepared by similar procedure.

Results

Comparative analyses of cord blood and corresponding digest of tissue placenta demonstrated that digested tissue of placenta yield similar or higher numbers of live CD45+ CD34+ cells. Percent of CD45+ CD34+ cells of granulocytes was 4-5 times higher in placenta tissue. Therefore, estimated total numbers of hematopoietic cells which are available from one placenta are on average an order of magnitude higher, compared to that from total cord blood sample. These results are illustrated in Table 1.

TABLE 1

| | Live CD34+ CD45+ cells | | |
|---|---|---|---|
| | Per ml or per gram | Percent of total nucleated cells counted | Total |
| Cord blood | $(0.7 \pm 0.3) \times 10^4$/ml | $0.06 \pm 0.2$ | $(0.7 \pm 0.3) \times 10^6$ in 100 ml |
| Placenta tissue | $(1.1 \pm 0.4) \times 10^4$/g | $0.34 \pm 0.1$ (P < 0.05) | $(0.7 \pm 0.2) \times 10^7$ in 600 g tissue |

Figure 1A:
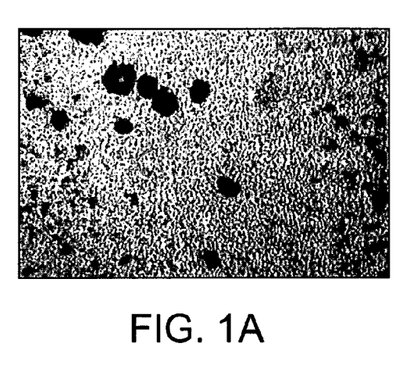
FIGS. 1A-C depict hematopoietic stem cells derived from term placenta and cord blood, differentiation assays and long-term culture-initiating cells.
Figure 1B:
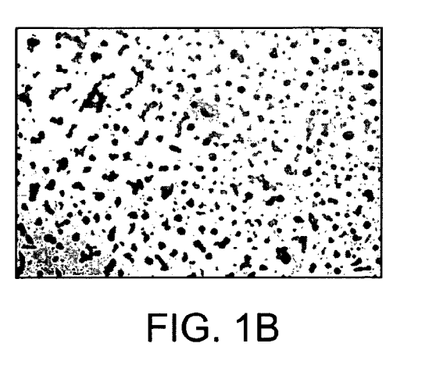
Figure 1C:
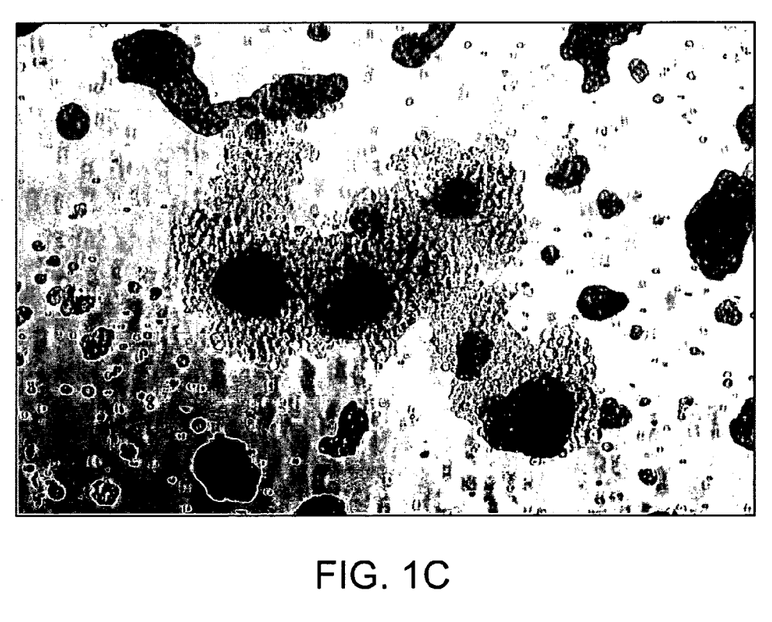

Placenta-derived hematopoietic cells were further evaluated for their ability to differentiate into blood cells by standard colony-forming analyses. Cells derived from placenta tissue produced a large number of colony-forming units, including CFU-E, BFU-E, CFU-GM, CFU-GEMM, similar to cord blood. Microscopic appearance of these colonies in illustrated in FIG. 1.

FIG. 1. Hematopoetic stem cells derived from term placenta and cord blood, differentiation assays and LTC-IC. Placenta-derived hematopoietic stem cells give rise to multiple lineages of blood cells. Microscopy images of colony-forming units derived from: A—cord blood (magnification× 10, CFU-E, BFU-E and CFU-GEMM are visible; B, C—digested placental tissue following perfusion/cryopreservation. B—magnification ×5, multiple CFU-E are present.

C—digested placental tissue, magnification ×40, CFU-E and CFU-GEMM are clearly visible.

Quantitative data for the amount of colony forming units obtained from placenta tissue digest as compared to corresponding cord blood unit are given in Table 2. Cells derived from placenta yield larger amounts of blood cells colony-forming units, than cord blood.

TABLE 2

|  | Cord Blood per $10^5$ cells | Placenta tissue per $10^5$ cells |
|---|---|---|
| CFU-E | 18 ± 6 | 111 ± 45 |
| BFU-E | 123 ± 28 | 240 ± 115 |
| CFU-GM | 172 ± 45 | 235 ± 121 |

Immunofluorescent staining of hematopoietic cells in term human placenta demonstrated presence of large numbers of cells clusters, positive for hematopoietic stem cells—CD34$^+$, CD117$^+$, CD133$^+$, CD38. The estimated numbers of these cells per whole placenta averaged $10^7$ cells per placenta. Examples of these clusters, located in loose connective tissue in perivascular regions of placenta and not associated with circulation, are given in FIG. 2-4.

Figure 2:
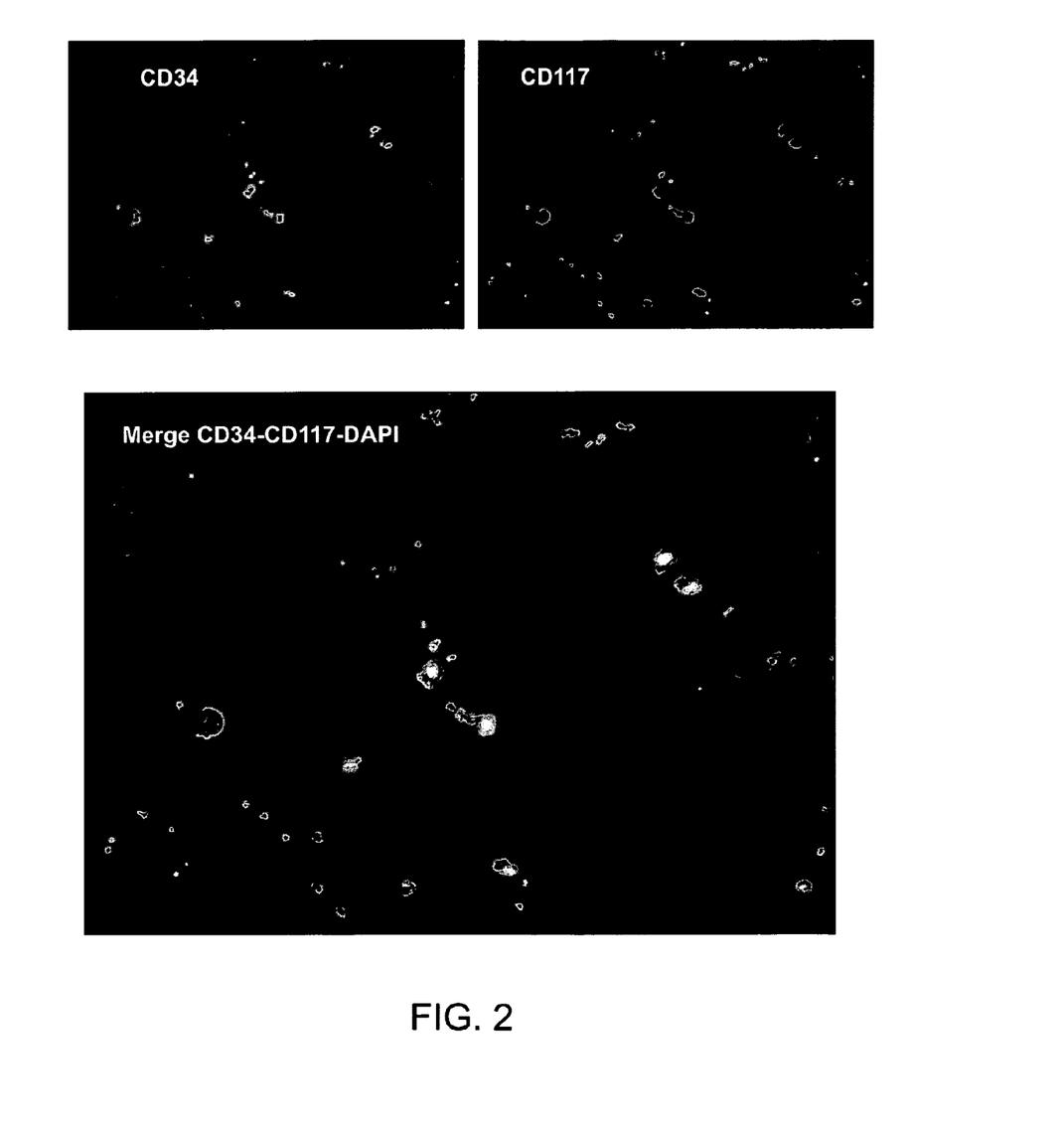
FIG. 2 depicts a paraffin section of human placenta, stained for CD34 and CD117.

FIG. 2. Paraffin section of human placenta, stained for CD34 (FITC-green) and CD117 (c-kit). (PE, red)—marker of hematopoietic cells. Nuclear staining DAPI (blue).

Figure 3:
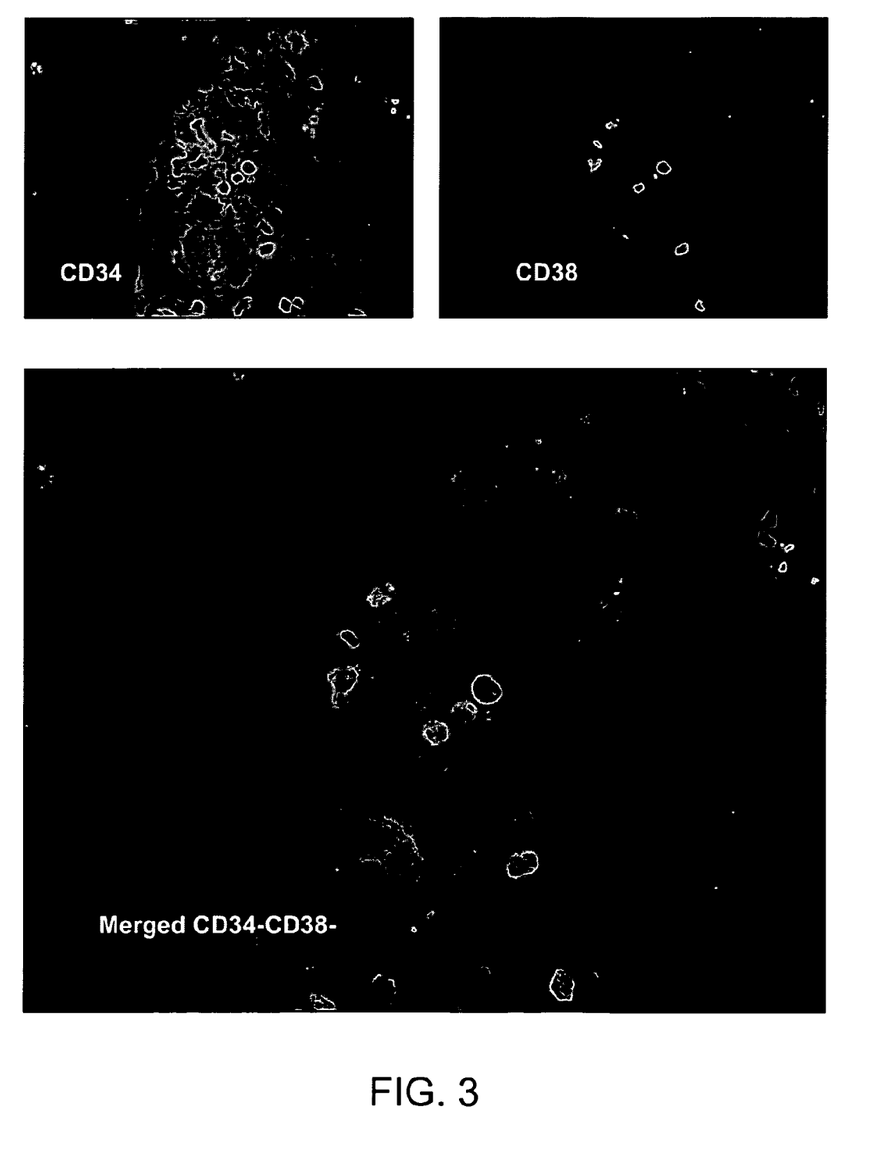
FIG. 3 depicts a paraffin section of human placenta stained for CD34 and CD38.

FIG. 3. Paraffin section of human placenta stained for CD34 (FITC-green) and CD38 (PE, red)—marker of hematopoietic cells. Nuclear staining DAPI (blue).

Figure 4:
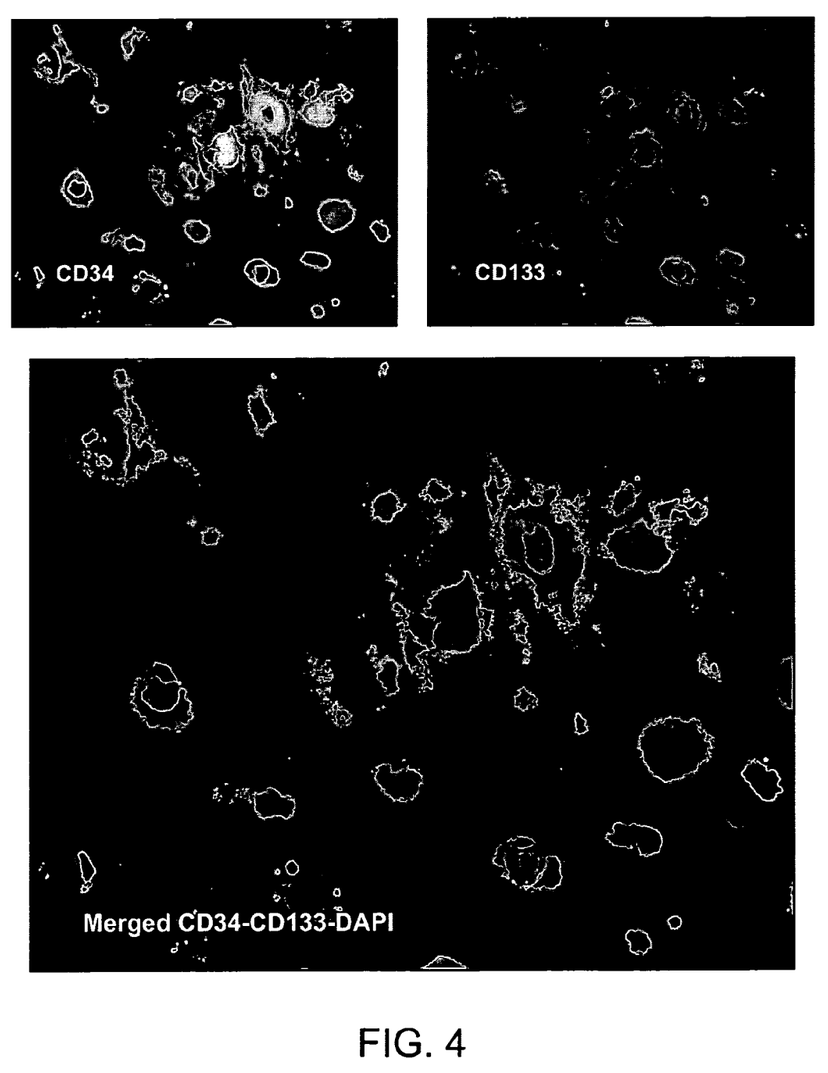
FIG. 4 depicts a paraffin section of human placenta, stained for CD34 and CD133.

FIG. 4. Paraffin section of human placenta, stained for CD34 (FITC-green) and CD133 (PE, red)—marker of hematopoietic cells. Nuclear staining DAPI (blue).

Perfusion of placenta with cryopreservatives allowed enhancing the survival of hematopoietic cells several-fold, as shown in Table 3. Perfusion also preserved the differentiation capacity of these cells, as illustrated in Table 4.

TABLE 3

|  | Cord Blood | Placenta tissue without perfusion with cryopreservatives | Placenta tissue following perfusion with cryopreservatives |
|---|---|---|---|
| Live CD34+ CD45+ cells per ml (per g for tissue) | (0.5 ± 0.1) × $10^4$ | (0.1 ± 0.1) × $10^4$ | (1.5 ± 0.1) × $10^4$ |
| Live CD34+ CD45+ cells Percent of total nucleated cells counted | 0.03 ± 0.1 | 0.03 ± 0.01 (P < 0.05) | 0.3 ± 0.1 (P < 0.05) |
| Total amount of live CD34+ CD45+ cells per total sample of cord blood (100 ml) or placenta (800 g) tissue) | (0.5 ± 0.1) × $10^6$ | (0.6 ± 0.2) × $10^6$ | (1.1 ± 0.4) × $10^7$ |

TABLE 4

|  | Cord Blood per $10^5$ cells | Placenta tissue per $10^5$ cells without perfusion with cryopreservatives | Placenta tissue per $10^5$ cells after perfusion with cryopreservatives |
|---|---|---|---|
| CFU-E | 8 ± 4 | 11 ± 5 | 123 ± 55 |
| BFU-E | 34 ± 13 | 42 ± 16 | 411 ± 58 |
| CFU-GM | 68 ± 51 | 25 ± 12 | 311 ± 72 |

Derivation and differentiation of stromal placenta-derived stem cells from cryopreserved placenta. Cryopreserved placentas allowed obtaining and propagating up to 30 passages plastic-adherent cells. Characterization of human placenta-derived stromal plastic-adherent "stem cells" demonstrated, that these cells are negative for CD45, CD34, CD38, SH2b (a marker of developing neurons). The rate of cell proliferation is very high, doubling time is about 8-10 hours. Some populations are medium-low positive for markers of human bone marrow mesenchymal stem cells (CD90, CD105), less than 10%. Cells are highly positive for Neurofilament-200 (marker of neurons). Nuclear localization of Neurofilament 200 (as seen in these cells) is a marker of embryonic neurons. Cells are highly positive for Oct-4 and SSEA-3, markers of human embryonic stem cells. Cells are highly positive for CD133—a marker of human pluripotent (hematopoietic, endothelial, neuronal and epithelial precursors) stem cells. Cells differentiate into adipocytes, osteoblasts and neurons.

These cells were used as feeder layers for non-adherent cells. Six week co-culture of hematopoietic progenitors on these feeder layers, with following culture of lufted cell in MethoCult medium allowed to determine numbers of LTC-IC. Perfusion of placenta with cryopreservatives allowed to enhance yield of LTC-IC from cryostored placenta, as illustrated in Table 5. Table 5 shows LTC-IC cultures of cord blood and cryopreserved placenta. Colony-forming capacity of cord blood and digests of placental tissue, following cryopreservation without and with perfusion of placenta. Perfusion significantly enhanced survival of LTC-ICs.

TABLE 5

|  | Cord Blood Per $10^4$ | Placenta tissue per $10^4$ cells without perfusion with cryopreservatives | Placenta tissue per $10^4$ cells after perfusion with cryopreservatives |
|---|---|---|---|
| CFU-E | 3 ± 1 | 1 ± 1 | 12 ± 5 |
| BFU-E | 4 ± 1 | 1 ± 1 | 11 ± 5 |
| CFU-GM | 6 ± 1 | 2 ± 2 | 10 ± 4 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of obtaining fetal stem and progenitor cells from a cryopreserved mammalian placenta, the method comprising:
    a) perfusing a cryopreserved mammalian placenta with a collection solution comprising an effective amount of an agent that induces mobilization of a stem and/or progenitor cell into a blood vessel of the placenta, wherein the mobilization agent is AMD-3100, a biocompatible non-ionic surfactant, an antibody that binds specifically to an adhesion molecule and that inhibits cell adhesion, a thrombolytic enzyme, or ethylenediamine tetraacetic acid; and b) collecting the mobilized cells from the blood vessel, wherein the collected cells comprise fetal stem and progenitor cells.

2. The method of claim 1, wherein the mobilization agent is a biocompatible non-ionic surfactant.

3. The method of claim 2, wherein the biocompatible non-ionic surfactant is tyloxapol.

4. The method of claim 1, wherein the agent that induces mobilization is AMD-3100.

5. The method of claim 1, wherein the collection solution comprises a cytokine that promotes maintenance of a stem cell or progenitor cell phenotype.

6. The method of claim 1, wherein the collection solution comprises two or more mobilization agents.

7. The method of claim 1, further comprising removing any residual maternal cells from the collected cells.

8. The method of claim 1, further comprising inducing differentiation of a collected fetal stem/progenitor cell in vitro, wherein said inducing results in differentiation of a collected fetal stem/progenitor cell into one or more differentiated cell types.

9. The method of claim 8, wherein the one or more differentiated cell type is an adipocyte, a hepatocyte, a oligodendrocyte, or a myeloid lineage cell.

10. The method of claim 1, wherein said collected stem/progenitor cells comprise hematopoietic stem cells.

11. The method of claim 1, wherein said collected stem/progenitor cells comprise mesenchymal stem cells.

12. The method of claim 1, wherein said collected stem/progenitor cells comprise placenta-derived multipotent cells.

13. The method of claim 1, wherein said collected stem and progenitor cells comprise from about $10^6$ to about $10^9$ viable fetal stem and progenitor cells.

14. The method of claim 1, wherein the biocompatible non-ionic surfactant is selected from diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octoxinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters.

15. The method of claim 1, wherein the antibody that binds specifically to a cell adhesion molecule and inhibits cell adhesion specifically binds an adhesion molecule selected from intracellular adhesion molecule, a vascular cell adhesion molecule, a platelet-endothelial cell adhesion molecule, an integrin, a cadherin, and a selectin.

16. The method of claim 1, wherein the thrombolytic enzyme is streptokinase or urokinase.

17. The method of claim 1, wherein the mobilization agent is AMD-3100.

18. The method of claim 5, wherein the cytokine is selected from colony-stimulating factor-1, granulocyte colony-stimulating factor, granulocyte-macrophage colony-stimulating factor, megakaryocyte colony-stimulating factor, interferon-α (IFN-α), consensus interferon, IFN-β, IFN-γ, IL-1α, IL-1β, IL-2, IL-3, IL-4, IL-5, IL-6, IL-10, IL-11, IL-13, a stem cell factor, leukemia inhibitory factor, oncostatin M, erythropoietin, and thrombopoietin.

* * * * *